United States Patent [19]

Turk

[11] Patent Number: 5,357,978
[45] Date of Patent: Oct. 25, 1994

[54] RAPID EXCHANGE GUIDEWIRE LOADING ATTACHMENT

[75] Inventor: Peter I. C. Turk, San Juan Capistrano, Calif.

[73] Assignee: Medtronic, Inc., Minneapolis, Minn.

[21] Appl. No.: 3,356

[22] Filed: Jan. 12, 1993

[51] Int. Cl.⁵ .................................. A61B 5/00
[52] U.S. Cl. ........................... 128/772; 128/11
[58] Field of Search .............. 128/10, 11, 17, 18, 128/657, 772

[56] References Cited

U.S. PATENT DOCUMENTS

| | | | |
|---|---|---|---|
| 1,201,550 | 10/1916 | Brush | 128/11 |
| 1,286,287 | 12/1918 | Glenn | 128/11 |
| 1,509,041 | 9/1924 | Hyams | 128/11 |
| 1,989,162 | 1/1935 | Barr | 128/11 |
| 3,005,452 | 10/1961 | Pitman | 128/11 |
| 3,789,835 | 2/1974 | Whitman | 128/18 |
| 4,323,071 | 4/1982 | Simpson | 128/343 |
| 4,748,982 | 6/1988 | Horzewski | 128/344 |
| 4,762,129 | 8/1988 | Bonzel | 128/344 |
| 4,824,435 | 4/1989 | Giesy et al. | 604/49 |
| 4,988,356 | 1/1991 | Crittenden | 606/192 |
| 5,038,766 | 8/1991 | Parker | 128/10 |
| 5,040,548 | 8/1991 | Yock | 128/898 |
| 5,046,497 | 9/1991 | Millar | 128/637 |
| 5,061,273 | 10/1991 | Yock | 606/194 |

*Primary Examiner*—Max Hindenburg
*Attorney, Agent, or Firm*—Dianne M. F. Plunkett; Harold R. Patton

[57] ABSTRACT

The disclosed device relates to over-the-wire PTCA balloon catheters (5), and more particularly, to a rapid exchange catheter (5) for dilatation therapy. The rapid exchange medical catheter (5) has a wire guiding means external to the shaft (35) for slidably mounting over the guidewire (70), the wire guiding means being at least two loops (15) and having a guidewire loading attachment (20) between each pair of loops. The guidewire loading attachment consists of a snap ring (45) depending from a tubular member (55) defining a guidewire lumen (50). The guidewire loading attachment (20) snaps on to the shaft (35) through a slot (60) in the loading attachment (20), the slot (60) having a diameter less than that of the shaft (35) resulting in a compression fit. The loading attachment (20) is removed after loading the guidewire (70).

7 Claims, 2 Drawing Sheets

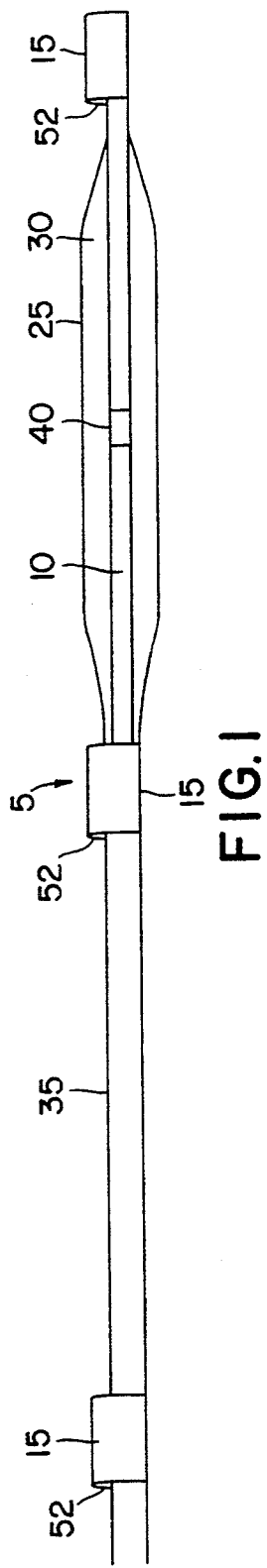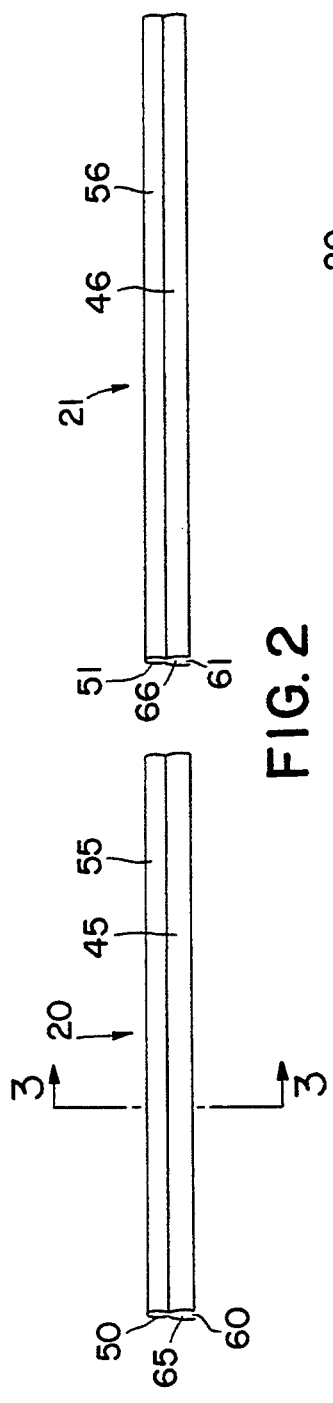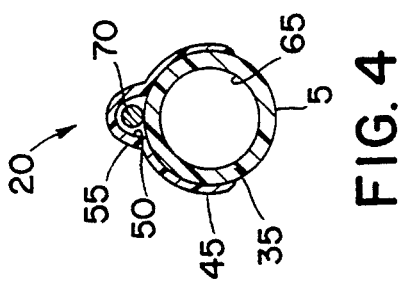

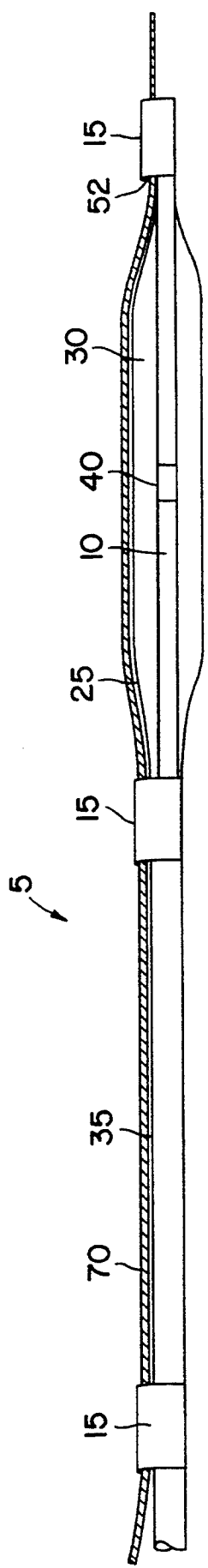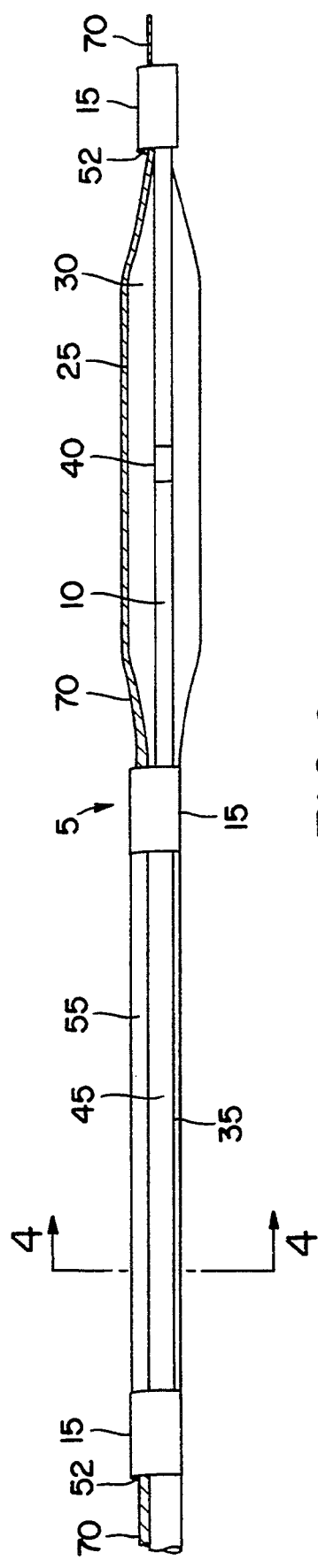

RAPID EXCHANGE GUIDEWIRE LOADING ATTACHMENT

BACKGROUND OF THE INVENTION

1. Field of the Invention

The present invention relates to rapid exchange over-the-wire PTCA balloon catheters, and more particularly, to catheters which are exchangeable over a guidewire.

2. Description of the Prior Art

This description of art is not intended to constitute an admission that any patent, publication or other information referred to is "prior art" with respect to this invention, unless specifically designated as such. In addition, this section should not be construed to mean that a search has been made or that no other pertinent information as defined in 37 C.F.R. § 1.56(a) exists.

Catheters comprise tube-like members inserted into the body for diagnostic or therapeutic medical reasons. One of the therapeutic procedures applicable to the present invention is known as percutaneous transluminal coronary angioplasty (PTCA). PTCA has evolved through three major stages, fixed wire systems, over-the-wire systems and rapid exchange systems. The first PTCA procedure was developed in approximately 1976–1977 by Dr. Andreas Gruntzig. This fixed wire system featured a core or guidewire fixed within the catheter to stiffen it so that it could be pushed into position in the vascular system. Blockage in a coronary artery could be reduced by positioning the balloon dilatation catheter across from the blockage and inflating the balloon causing the blockage to decrease.

In 1980–1981, Dr. John Simpson began to modify the fixed wire system developing an over-the-wire catheter with a free central lumen for movable guide wires and with a dilatation balloon formed from the outer surface covering in a unitary, that is, one-piece construction. This catheter system is the subject of U.S. Pat. No. 4,323,071. Using such a movable wire system, one could more readily select the desired coronary artery and reach smaller branches as movable guide wires are inherently smaller and more flexible than the fixed wire systems.

If a catheter must be exchanged for one of a different size, the over-the-wire system is advantageous because the guidewire can be left in place. The catheter is withdrawn over the guidewire and another catheter slid into place over it. A disadvantage of this exchange procedure is that it is difficult to keep the guidewire in place, since removing the catheter requires removal of the guidewire and subsequent recrossing of the stenosis. Alternatively a very long "exchange" guidewire of approximately 300 cm can be used. This is difficult to handle because such a procedure requires two operators who must be in communication during the procedure. This requires more time and risks contamination by dropping the guidewire from the sterile field. An alternative to these long exchange guidewires is a two-part guidewire. This is also undesirable because it requires additional time to assemble and may be too thick to allow smooth exchanges.

Rapid exchange catheters were developed to respond to the disadvantage of the long "exchange" wire in over-the-wire systems. These catheters have shorter guidewire lumens passing through the balloon so that the guidewire exits from the catheter closer to the balloon than to the proximal end of the catheter. This enables the physician to anchor or hold the guidewire as he or she removes the catheter from the body with the exchange occurring over the shorter guidewire lumen.

One of the first rapid exchange catheters was U.S. Pat. No. 4,762,129 issued to Bonzel. A disadvantage of this catheter is that the position of the guidewire exit port at the proximal balloon bond coupled with a short guidewire exchange lumen, as in the Bonzel construction, can cause the balloon to become snagged during withdrawal through the tortuous path. The resultant buckling of the catheter may result in inadvertent withdrawal of the guidewire from the lesion due to seizure of the guidewire by the buckled lumen.

Rapid exchange catheter designs such as those in Yock, U.S. Pat. Nos. 5,040,548 and 5,061,273, responded to the problem of catheter buckling and inadvertent guidewire withdrawal by lengthening the guidewire exchange lumen. In Yock, the guidewire lumen passes through the balloon and is generally coaxial with respect to the inflation lumen, but exits (or enters) in the side port at least 10 centimeters from the distal tip of the catheter. The Yock disclosure suggests a lumen of 10 or more centimeters; in catheters on the market, the lumen varies from about 9 to 35 centimeters in length. The lengthened guidewire lumen, however, induces friction between the catheter and guidewire during catheter manipulation and withdrawal. Such friction can contribute to extraneous guidewire movement.

Other versions of rapid exchange catheters are shown in the following patents: U.S. Pat. No. 4,748,982 issued to Horzewski, et al., and U.S. Pat. No. 4,988,356 issued to Crittenden. Here the guidewire lumen contains a slit extending its length (except where it passes through the balloon) so that the guidewire can be removed from the lumen through the slit at a point immediately proximal to the balloon. The lengthened guidewire lumen induces friction between the catheter and guidewire during catheter manipulation and withdrawal. Such friction can contribute to extraneous guidewire movement.

U.S. Pat. No. 4,824,435 to Giesy and U.S. Pat. No. 5,046,497 to Millar represent another variety of catheters, those for instrument delivery. Giesy discloses a method and apparatus for guiding diagnostic and therapeutic devices into tortuous body passages. A secondary guidewire 12 has a guide loop 10 comprising a member which may be threaded over a primary guidewire 14. This allows passage of an instrument over the guidewire 14 without the use of a through-lumen. The guide loop 10 is positioned at the tip or distal end of the instrument. The instrument is advanced alongside the guide wire 14 and is kept on course via the secondary guide wire 12 pushing behind the instrument.

U.S. Pat. No. 5,046,497 to Millar discloses a relatively short coupling structure (eg. 1 cm) slidably engaging the guidewire (see col. 3, lns. 14–17) allowing a plurality of diagnostic or therapeutic catheters such as sensor-carrying catheters which can be simultaneously coupled to a common guidewire (col. 1, lns. 15–22). Previously inserted devices need not be removed before insertion of subsequent devices.

Co-pending patent application Serial No. 07/859,769 to Buchbinder et al. discloses an over-the-wire catheter which provides support for the guidewire in multiple locations using rapid exchange loops along the catheter. Given the spacing of the rapid exchange loops, difficulties arise in threading the guidewire through them as each loop must be threaded individually. To facilitate threading the guidewire through the catheter rapid exchange loops, a loading attachment is needed. The guidewire loading attachment of the present invention is designed to snap on to the catheter shaft between pairs of such loops.

SUMMARY OF THE INVENTION

The present invention in one aspect discloses a rapid exchange medical catheter having a wire guiding means external to the shaft for slidably mounting over the guidewire, the wire guiding means being multiple rapid exchange loops. In the preferred embodiment, a loading attachment snaps on over the catheter body between each pair of rapid exchange loops. The loading attachment comprises a snap ring which depends from a tubular member defining a guidewire lumen and a slot in the snap ring having a width less than the diameter of the shaft to enable a compression fit of the snap ring upon the shaft. The guidewire loading attachment consists of biocompatible materials which are flexible yet semi-stiff such as polymers like polyethylene or polypropylene. After the guidewire is threaded through the continuous lumen now formed by the rapid exchange loops and guidewire loading attachment, the guidewire loading attachment is removed, then the catheter and guidewire are inserted together into the vessel.

BRIEF DESCRIPTION OF THE DRAWINGS

FIG. 1 represents a fragmentary longitudinal view of a catheter with 3 rapid exchange loops;

FIG. 2 represents the longitudinal view showing the positioning of two guidewire loading attachments above FIG. 1 before the loading attachment is snapped on;

FIG. 3 represents the cross-sectional view along the line 3—3 of the guidewire loading attachment;

FIG. 4 represents the cross-sectional view along the line 4—4 of FIG. 6 of the catheter with loading attachment affixed;

FIG. 5 represents a fragmentary longitudinal view of a catheter with 3 rapid exchange loops and a guidewire loaded between them.

FIG. 6 represents the catheter of FIG. 1 with one loading attachment of FIG. 2 snapped on.

DETAILED DESCRIPTION OF THE PREFERRED EMBODIMENTS

The preferred embodiment of the present invention includes a rapid exchange catheter having a wire guiding means external to the shaft for slidably mounting over the guidewire, the wire guiding means being multiple rapid exchange loops. A loading attachment snaps on over the catheter body between each pair of rapid exchange loops. The loading attachment comprises a snap ring which depends from a tubular member defining a guidewire lumen and a slot in the snap ring having a width less than the diameter of the shaft to enable a compression fit of the snap ring upon the shaft. The guidewire loading attachment consists of biocompatible materials which are flexible yet semi-stiff such as polymers like polyethylene or polypropylene. After the guidewire is threaded through the continuous lumen now formed by the rapid exchange loops and guidewire loading attachment, the guidewire loading attachment is removed, then the catheter and guidewire are inserted together into the vessel.

An object of Applicant's invention is to facilitate guidewire loading and to reduce friction as the catheter is threaded through the vascular system. Given the spacing of the rapid exchange loops, difficulties arise in loading the guidewire through them as each loop must be threaded individually. To facilitate threading the guidewire through the catheter rapid exchange loops, a loading attachment is needed. The guidewire loading attachment snaps on the catheter between two rapid exchange loops and can be supplied preattached to the catheter. Once the guidewire is loaded, the loading attachment is removed thereby reducing friction as the catheter is threaded through tortuous passages.

The guidewire loading attachment of the invention may be used with a catheter having a therapy means such as a dilatation catheter having a balloon at the distal end which can be placed across a stenosis. Under fluoroscopic guidance, the guidewire can be placed first in proximity to a stenosis and then across the stenosis. The rapid exchange balloon dilatation catheter can then be inserted into the stenosis following the path established by the guidewire. Further manipulations of the catheter are made to position the device across the obstruction. If successfully placed, the balloon is inflated in such a manner that the diameter of the obstructed area is increased.

Frequently in PTCA, multiple catheters must be sequentially applied during a procedure. The average number of catheters used per patient procedure is 1.6. Once a stenosis has been crossed and dilated with the dilating balloon, the dilatation catheter can be withdrawn, leaving the guidewire in position across the stenosis. A different device can then be inserted over the guidewire, as for example, an intervascular ultrasound device, an angioscopy device, a fiber optic viewing catheter, an arterial stent delivery catheter, or another dilatation catheter to further enlarge the cross sectional diameter of the obstruction by means of repeated dilatation with a balloon of greater diameter. Additionally, it may be desirable for the physician to be able to place the guidewire across another obstruction and to dilate this with a balloon dilatation catheter having a balloon of a different diameter.

The invention can be better understood by referring to the drawings in FIGS. 1–6. The balloon catheter 5 can be made in any conventional manner and could consist of the following general elements, a shaft 35, core wire 10, radiopaque marker band 40, rapid exchange loops 15, balloon 25 and balloon inflation lumen 30. The central core wire 10 is made of any biocompatible material, preferably of #304 stainless steel. The core wire 10 provides stiffness which improves pushability and torquability. The core wire 10 extends throughout the length of the catheter 5. The balloon 25 is made of biocompatible material such as low density polyethylene and is mounted to the catheter shaft 35 at the balloon 25 proximal end and to the core wire 10 at the distal end. Balloon inflation liquids are perfused through the balloon inflation lumen 30.

A radiopaque marker band 40 is bonded to the core wire 10, preferably at the point which is the center of the balloon 25, although it could be located other places such as the proximal and/or distal ends of the balloon 25. The marker band 40 is used to provide a fluoroscopic indication of the location of the balloon 25 thereby allowing the operator to adjust the position of the balloon 25. Preferred materials for the marker band 40 include 100% gold, 100% iridium, or alloys of these materials such as a Pt-It alloy consisting of 90% platinum and 10% iridium. The preferred density is of at least 19.3 to 21.0 gm/cm³.

The rapid exchange loops 15 are mounted external to the catheter shaft 35 and spaced apart from the therapy means or balloon 25. The loops 15 form a guidewire lumen 52 for slidably inserting a guidewire 70. The rapid exchange loops 15 are preferably mounted on one side of the catheter shaft 35. The loops 15 can all be mounted proximally to the balloon 25 or one loop 15 can be mounted distally to the balloon 25 and the balance of the loops 15 mounted proximally to the balloon 25. The loops 15 can be affixed by heat shrinking or by glue, such as cyanoacrylate, to the shaft 35. The guidewire 70 may be more pushable and track better as the length of the loops 15 increase. Suitable lengths range from one to two cm.

A typical balloon 25 has the following length, diameter and material characteristics. Balloon length ranges from 2 cm to 4 cm with diameter size ranging from 1.5 mm to 5.0 mm. The balloon 25 is made of a biocompatible material such as low density polyethylene or similar materials which have a known diameter under a specific pressure. The distal end of the Balloon 25 is heat shrunk to the distal end of the core wire 10.

Applicant's catheter material for all embodiments comprises any biocompatible polymer or metal. Polymers include polyimide and more preferably polyethylene which is clear. A clear radiolucent material is preferable because air bubbles visible during the purging process alert the operator to malfunction. In the preferred embodiment, only the radiopaque marker band 40 is not clear.

FIG. 6 represents the catheter of FIG. 1 with the loading attachment of FIG. 3 snapped on.

The rapid exchange guidewire loading attachment 20 consists of a snap ring 45 or 46 which depends from a tubular member 55 or 56 defining a guidewire lumen 50 or 51. The snap ring 45 or 46 has a slot 60 generally opposite the tubular member 55 or 56. The slot 60 or 61 opening is of a distance which is less than the diameter of the catheter shaft 35 resulting in a compression fit which precludes accidental removal of the guidewire loading attachment 20 or 21 from the shaft 35. The guidewire loading attachment 20 or 21 snaps on the catheter shaft 35 between two rapid exchange loops 15. The loading attachment 20 or 21 can be made of any biocompatible materials which are flexible yet semi-stiff such as polymers which permit the distal ends of the snap ring 45 or 46 to be spread apart and the catheter shaft 35 inserted through the slot 60 or 61 and into the shaft lumen 65 or 66. For example, polyethylene or polypropylene can be used. The loading attachment 20 or 21 is an open ended extruded profile which is cut into discrete lengths and supplied attached to the catheter 5. Once the guidewire 70 is loaded into the guidewire lumen 50 or 51, the guidewire loading attachment 20 or 21 is removed and discarded.

The preceding specific embodiment is illustrative of the practice of the invention. It is to be understood, however, that other expedients known to those skilled in the art or disclosed herein, may be employed without departing from the spirit of the invention or the scope of the appended claims.

| No. | Component |
| --- | --- |
| 5 | Catheter |

-continued

| No. | Component |
| --- | --- |
| 10 | Core Wire |
| 15 | Rapid Exchange Loop |
| 20,21 | Guidewire Loading Attachment |
| 25 | Balloon |
| 30 | Balloon Inflation Lumen |
| 35 | Shaft |
| 40 | Radiopaque Marker Band |
| 45,46 | Snap Ring |
| 50,51 | Guidewire Lumen |
| 52 | Loop Guidewire Lumen |
| 55,56 | Tubular member |
| 60,61 | Slot |
| 65,66 | Shaft Lumen |
| 70 | Guidewire |

What is claimed is:

1. A catheter comprising:

an elongated shaft having a proximal end and a distal end;

a therapy means for providing medical treatment, the therapy means being mounted generally adjacent to the distal end of the shaft;

a wire guiding means mounted external to the shaft for slidably mounting over a guidewire, the wire guiding means being at least two loops; and a guidewire loading attachment extending between each pair of loops to facilitate loading of the guidewire into said wire guiding means, the loading attachment comprising:

a snap ring depending from a tubular member defining a guidewire lumen and a slot in the snap ring, the slot having a width less than the diameter of the shaft to enable a compression fit of the snap ring upon the shaft.

2. The catheter of claim 1 wherein the guidewire loading attachment materials consist of biocompatible materials which are flexible yet semi-stiff.

3. The catheter of claim 2 wherein the guidewire loading attachment materials consist of polymers.

4. The catheter of claim 3 wherein the guidewire loading attachment materials consist of polyethylene or polypropylene.

5. A catheter according to claim 1 wherein the therapy means is an balloon.

6. A method of inserting a catheter on a guidewire comprising:

providing a catheter with an angioplasty balloon having at least two guidewire loops, the first loop proximal to the second loop and a guidewire loading attachment between each pair of loops, the loading attachment comprising a snap ring depending from a tubular member defining a guidewire lumen and a slot in the snap ring, the slot having a length less than the diameter of the shaft to enable a compression fit of the snap ring upon the shaft;

inserting the guidewire through the first loop, then through the loading attachment, then through the second loop and finally through any successive pairs of loops and loading attachments;

removing all guidewire loading attachment(s);

inserting the catheter and guidewire in a human body; and allowing the catheter to be withdrawn over the loops while maintaining access to a vessel being treated by keeping the guidewire in place in the vessel.

7. A catheter comprising:

an elongated shaft having a proximal end and a distal end;

a wire guiding means mounted external to the shaft for slidably mounting over a guidewire, the wire guiding means being at least two loops; and a guidewire loading attachment extending between each pair of loops, to facilitate loading of the guidewire into said wire guiding means the loading attachment comprising;

a snap ring depending from a tubular member defining a guidewire lumen and a slot in the snap ring, the slot having a width less than the diameter of the shaft to enable a compression fit of the snap ring upon the shaft. guidewire, the wire guiding means being at least two loops; and a guidewire loading attachment extending between each pair of loops to facilitate loading of the guidewire into said wire guiding means, the loading attachment comprising;

a snap ring depending from a tubular member defining a guidewire lumen and a slot in the snap ring, the slot having a width less than the diameter of the shaft to enable a compression fit of the snap ring upon the shaft.

* * * * *

UNITED STATES PATENT AND TRADEMARK OFFICE
CERTIFICATE OF CORRECTION

PATENT NO. : 5,357,978
DATED : October 25, 1994
INVENTOR(S) : Peter I.C. Turk

It is certified that error appears in the above-indentified patent and that said Letters Patent is hereby corrected as shown below:

Column 8, Line 1 (Claim 7) delete all text after "...upon the shaft." (about three paragraphs)

Signed and Sealed this

Tenth Day of January, 1995

Attest:

BRUCE LEHMAN

*Attesting Officer*     *Commissioner of Patents and Trademarks*